(12) United States Patent
Varma

(10) Patent No.: US 8,310,679 B2
(45) Date of Patent: Nov. 13, 2012

(54) APPARATUS AND METHODS FOR SENSING OR IMAGING USING STACKED THIN FILMS

(75) Inventor: Manoj Varma, Bangalore (IN)

(73) Assignee: Indian Institute of Science, Karnataka (IN)

( * ) Notice: Subject to any disclaimer, the term of this patent is extended or adjusted under 35 U.S.C. 154(b) by 0 days.

(21) Appl. No.: 13/318,601

(22) PCT Filed: Mar. 17, 2011

(86) PCT No.: PCT/IB2011/051120
§ 371 (c)(1),
(2), (4) Date: Nov. 2, 2011

(87) PCT Pub. No.: WO2012/104680
PCT Pub. Date: Aug. 9, 2012

(65) Prior Publication Data
US 2012/0194819 A1    Aug. 2, 2012

(51) Int. Cl.
*G01N 21/55* (2006.01)
(52) U.S. Cl. ........ 356/445; 356/369; 356/419; 436/501; 422/82.05
(58) Field of Classification Search ......... 356/445–448, 356/364–369, 71, 416, 419; 422/55, 82.05, 422/82.11; 435/287.1; 436/501
See application file for complete search history.

(56) References Cited

U.S. PATENT DOCUMENTS

| | | | |
|---|---|---|---|
| 6,907,057 B2 | 6/2005 | Shigihara et al. | |
| 7,706,057 B2 * | 4/2010 | Van Herpen et al. | 359/359 |
| 7,941,025 B2 * | 5/2011 | Shigihara | 385/131 |
| 2005/0002037 A1 * | 1/2005 | Harrison | 356/445 |
| 2006/0115227 A1 | 6/2006 | Shigihara | |
| 2007/0212257 A1 | 9/2007 | Nolte et al. | |
| 2008/0131693 A1 * | 6/2008 | Hiruma et al. | 428/336 |
| 2009/0148955 A1 * | 6/2009 | Cunningham et al. | 436/164 |
| 2009/0221096 A1 * | 9/2009 | Torres | 436/501 |
| 2010/0141948 A1 * | 6/2010 | Cohen et al. | 356/369 |
| 2011/0222066 A1 * | 9/2011 | Forcales et al. | 356/445 |

OTHER PUBLICATIONS

International Search Report dated Jun. 29, 2011 for PCT application Serial No. PCT/IB2011/051120.
R. Jenison et al, "Interference-based Detection of Nucleic Acid Targets on Optically Coated Silicon". Nat. Biotech. Jan. 2001, 19, 62-65.
G. Gauglitz, "Multiple Reflectance Interference Spectroscopy Measurements made in Parallel for Binding Studies", Rev. Sci. Instr. 2005, 76, 062224 (10 pages).
T. Gao et al, "Biomolecular Sensing Using Near-Null Single Wavelength Arrayed Imaging Reflectometry", Anal. Chem, 2006, 78, 6622-6627.
T. Gao et al., "Label-Free Sensing of Binding to Microarrays Using Brewster Angle Straddle Interferometry", Anal. Chem., 2007, 79, 7589-7595.
E. Ozkumur, et al., Label-free and Dynamic Detection of Biomolecular Interactions for High-Throughput Microarray Applications. PNAS, 2008, 105, 7988-7992.

(Continued)

*Primary Examiner* — Hoa Pham
(74) *Attorney, Agent, or Firm* — Foley & Lardner LLP

(57) ABSTRACT

Technologies are generally described for methods and systems for sensing or imaging. The apparatus includes a stack of a plurality of thin films, such as polymer thin films. The stack has a substantially imaginary total reflectance coefficient.

18 Claims, 8 Drawing Sheets

OTHER PUBLICATIONS

X. Wang et al., "Land-Contrast Self-Referencing Interferometric Protein Microarray", App. Phys. Lett., 2008, 93, 223904 (4 pages).
D. Nolte, "Review of Centrifugal Microfluidic and Bio-Optical Disks", Rev. Sci. Instr., 2009, 80, 101101 (22 pages).
X. Wang et al., "Prostate-Specific Antigen Immunoassays on the BioCD", Anal. Bioanal, Chem. 2009, 393, 1151-1156.
E. Ozkumur et al., "Quantification of DNA and Protein adsorption by Optical Phase Shift", Biosens. Bioelec. 2009, 25, 167-172.
R. Ince et al., "Analysis of the Performance of Interferometry, Surface Plasmon Resonance and Luminescence as Biosenesors and Chemosensors". Anal. Chem. Acta, 2006, 569, 1-20.
P. Yager et al., "Point-of-Care Diagnostics for Global Health", Annu. Rev. Biomed. Eng., 2008, 10, 107-144.
C. Chin et al., "Lab-On-A-Chip Devices for Global Health: Past Studies and Future Opportunities", Lab Chip, 2007, 7, 41-57.
C. Liu, "Recent Developments in Polymer MEMS", Adv. Mater., 2007, 19, 3783-3790.
G. Decher, "Fuzzy Nanoassemblies: Toward Layered Polymeric Multicomposites", Science, 1997, 277, 1232-1237.
A. Kabashin et al., "Phase and Amplitude Sensitivities in Surface Plasmon Resonance Bio and Chemical Sensing", Optics Express, 2009, 17, 23: 21191-21204.
J. Hiller et al., "Reversibly Erasable Nanoporous Anti-Reflection Coatings from Polyelectrolyte Multilayers" Nat. Matter. 2002, 1, 59-63.
J. Kim et al., "Design of a Thin Film for Optical Applications, Consisting of a High and Low Refractive Index Multilayers, Fabricated by a Layer-by-layer Self-assembly Method", Colloids and Surfaces A: Physicochem. Eng. Aspects, 2006, 284, 290-294.
R. Jenison et al., "Thin-film Technology for Direct Visual Detection of Nucleic Acid Sequences: Applications in Clinical Research," Expert Rev. Mol. Diagn. vol. 6(1), pp. 89-99.
R. Jenison et al., "Interference-based detection of nucleic acid targets on optically coated silicon," Nat. Biotechnol. vol. 19 (2001) pp. 62-65.
R. Jenison et al., "Silicon-based Biosensors for Rapid Detection of Protein or Nucleic Acid Targets," Clin. Chem. vol. 47:10 (2001), pp. 1894-1900.

* cited by examiner

APPARATUS AND METHODS FOR SENSING OR IMAGING USING STACKED THIN FILMS

CROSS REFERENCE TO RELATED APPLICATIONS

This application is a national stage entry of PCT/IB2011/051120, filed Mar. 17, 2011 which in turn claims priority to Indian Application No. 288/CHE/2011, filed Jan. 31, 2011. The entire contents of each of the foregoing applications are incorporate herein by reference.

TECHNICAL FIELD

The present disclosure is directed to apparatus and methods for sensing or imaging, particularly sensors or imagers comprising stacked thin films.

BACKGROUND

Unless otherwise indicated herein, the materials described in this section are not prior art to the claims in this application and are not admitted to be prior art by inclusion in this section.

Sensors and imagers are used in many different applications, and employ signals such as electromagnetic (EM) radiation to sense or image a composition or other properties of a sample. The EM radiation can be in infrared, optical, ultraviolet, or other wavelength regimes.

In recent years, highly multiplexed bio-molecular sensors are employed for the development of integrative or systems biology where a large number of genomic or proteomic variables are quantified to infer their interdependences. Such sensing technologies can also aid diagnosis of diseases through the detection of molecular markers of disease states.

Biosensors are employed in a variety of areas including pathogen detection and home diagnosis.

SUMMARY

In one aspect, an apparatus is provided for sensing or imaging with light at a wavelength $\lambda$. The apparatus includes a stack including a plurality of thin films. The stack has a substantially imaginary total reflectance coefficient for the light at the wavelength $\lambda$.

In one embodiment, the plurality of thin films include polymer thin films.

In one embodiment, the plurality of thin films include a plurality of bi-layers, wherein each of the plurality of bi-layers comprises a layer of high refractive index and a layer of low refractive index.

The stack can further include a top layer and a substrate. In one embodiment, the top layer has a refractive index $(n_l)$, a thickness $(d_l)$, and a reflectance $(r_l)$ selected such that they satisfy the following equations:

$$r'_s = \frac{r_s - r_l}{1 - r_s r_l} \text{ and } r_{net} = \frac{r_l + r'_s e^{-j2\phi_l}}{1 + r_l r'_s e^{-j2\phi_l}} = \pm j\beta$$

$$\frac{[r'_s(1+r_l^2)]^2 - [r_l(1+r'^2_s)]^2}{(1-r_l^2 r'^2_s)^2} = \beta^2$$

$$\cos\left(4\pi \frac{n_l d_l}{\lambda}\right) = -\left(\frac{r_l}{r'_s}\right)\left(\frac{1+r'^2_s}{1+r_l^2}\right)$$

wherein $\beta$ is an amplitude of a total reflectance coefficient $r_{net}$ of the stack including the top layer, wherein the total reflectance coefficient is imaginary and has a form of $\pm j\beta$, wherein $j$ is the imaginary unit and $\pm j = \sqrt{-1}$, and $r_s$ and $r'_s$ are the reflectance of the substrate and the plurality of bi-layers combined, calculated with air and the top layer as the ambient medium, respectively.

In one embodiment, the substrate is glass, polycarbonate, or polystyrene. The top layer can include poly (methyl methacrylate). The substrate can have a refractive index of about 1.6. In one example, the top layer has a refractive index of about 1.5.

In one embodiment, the plurality of thin films include organic thin films. In one example, the stack consists essentially of organic materials. The stack can consist essentially of polymers. In one embodiment, the stack contains substantially no inorganic semiconductor or semiconductor oxide.

In one embodiment, the plurality of thin films include a plurality of bi-layers, wherein each of the plurality of bi-layers comprises a layer of high refractive index and a layer of low refractive index. The high refractive index can be about 1.45-1.65, and the low refractive index is lower than the high refractive index. In one example, the high refractive index is about 1.6, and the low refractive index is about 1.5.

In one embodiment, the layer of high refractive index and the layer of low refractive index each have a thickness of approximately ¼ of the wavelength $\lambda$. The light can include one of a millimeter wave, an infrared, an optical, or an ultraviolet radiation. The apparatus can further include a light source configured to emit the light toward a sample to be sensed wherein the sample is disposed over the stack, and a photodetector configured to receive reflected light from the sample and the stack.

In one embodiment, the apparatus further includes an array of stacks each having a substantially imaginary reflectance at the wavelength $\lambda$, wherein the array is configured to sense a plurality of samples.

In one example, the plurality of thin films include at least four layers of thin films.

In one embodiment, the apparatus is configured to sense a sample disposed over the stack through a change in reflectance caused by the presence of the sample. The sample can include a biological sample, and wherein the apparatus is configured as a biosensor.

The sample can include a chemical material, and the apparatus can be configured as a chemical sensor. In another example, the sample includes an optical material, and the apparatus is configured as a color sensor.

In one embodiment, the stack has a purely imaginary reflectance, and the stack is configured to have an optimal signal-to-noise ratio in a reflected signal. In one embodiment, the plurality of thin films each have a purely real refractive index. In one embodiment, the stack includes polycarbonate and poly (methyl methacrylate). In one embodiment, the plurality of thin films have alternately high and low refractive indices with a difference of at least 0.1.

In one embodiment, the apparatus further includes a laser as a light source configured to illuminate a sample to be sensed, and a photodetector configured to detect reflected light from the sample, wherein the apparatus is configured to sense the sample based on a change in reflectance of the stack caused by the sample disposed over the stack.

In one embodiment, the apparatus is configured to image a sample disposed over the stack through a change in reflectance caused by the sample, wherein the sample comprises at least one of a biological layer, a non-biological layer, or a nano-scale thin film.

In another aspect, a stack is provided including a plurality of thin films, wherein the stack has a purely imaginary total reflectance for light at a wavelength $\lambda$.

In one embodiment, the plurality of thin include comprise organic thin films.

In one embodiment, the plurality of thin films include polymer thin films. In one example, the stack consists essentially of organic materials. In another example, the stack consists essentially of polymers. In another example, the stack contains substantially no inorganic semiconductor or semiconductor oxide.

In one embodiment, the plurality of thin films include a plurality of bi-layers, wherein each of the plurality of bi-layers comprises a layer of high refractive index and a layer of low refractive index. For example, the high and low refractive indices have a difference of at least 0.1. In one embodiment, the high and low refractive indices are in a range of about 1.45-1.65. In one embodiment, the high refractive index is about 1.6, and the low refractive index is about 1.5.

In one embodiment, the layer of high refractive index and the layer of low refractive index each have a thickness of approximately ¼ of the wavelength $\lambda$ of the light, and wherein the light is used for sensing a sample and comprises one of a millimeter wave, an infrared, an optical, or an ultraviolet radiation.

In one embodiment, the stack further includes a top layer and a substrate. The substrate can have a cost of less than $200/m². For example, the substrate is one of glass, polycarbonate, or polystyrene. The top layer can include poly (methyl methacrylate).

In one example, the substrate has a refractive index in a range of about 1.45-1.65. For example, the substrate can have a refractive index of about 1.6. The top layer can have a refractive index in a range of about 1.45-1.65. In one example, the top layer has a refractive index of about 1.5.

In one embodiment, the top layer has a refractive index ($n_l$), a thickness ($d_l$), and a reflectance ($r_l$) selected such that they satisfy the following equation:

$$r'_s = \frac{r_s - r_l}{1 - r_s r_l} \text{ and } r_{net} = \frac{r_l + r'_s e^{-j2\phi_l}}{1 + r_l r'_s e^{-j2\phi_l}} = \pm j\beta$$

$$\frac{[r'_s(1+r_l^2)]^2 - [r_l(1+r'^2_s)]^2}{(1-r_l^2 r'^2_s)^2} = \beta^2$$

$$\cos\left(4\pi \frac{n_l d_l}{\lambda}\right) = -\left(\frac{r_l}{r'_s}\right)\left(\frac{1+r'^2_s}{1+r_l^2}\right)$$

wherein $\beta$ is an amplitude of a total reflectance coefficient $r_{net}$ of the stack including the top layer, wherein the total reflectance coefficient is imaginary and has a form of $\pm j\beta$, wherein j is the imaginary unit and $\pm j=\sqrt{-1}$, and $r_s$ and $r_s'$ are the reflectance of the substrate and the plurality of bi-layers combined, calculated with air and the top layer as the ambient medium, respectively, and wherein $\lambda$ is the wavelength of the light used for imaging or sensing.

In one example, the plurality of thin films include at least four layers of thin films. In one embodiment, the stack has a purely imaginary reflectance. The stack can be configured to have an optimal signal-to-noise ratio in a reflected signal.

In one embodiment, the plurality of thin films each have a purely real refractive index. The stack can include at least one of polycarbonate, polystyrene, glass, or poly (methyl methacrylate). For example, the stack can include polycarbonate and poly (methyl methacrylate).

In one embodiment, the plurality of thin films have alternately high and low refractive indices with a difference of at least 0.1.

In one aspect, a method of making a sensor or an imager is provided. The method includes selecting materials for a top layer, a plurality of thin films, and a substrate, and forming a stack with the top layer, the plurality of thin films, and the substrate. The materials can be selected such that stack has a substantially imaginary total reflectance for light at a wavelength $\lambda$ used for imaging or sensing.

In one embodiment, the plurality of thin films include polymer thin films. The forming can include one of spin coating, electrostatic layer-by-layer self assembly, inkjet printing, extrusion, or screen printing.

In one embodiment, the forming includes disposing the plurality of thin films as a plurality of bi-layers, wherein each of the plurality of bi-layers comprises a layer of high refractive index and a layer of low refractive index. The layer of high refractive index and the layer of low refractive index each can have a thickness of approximately ¼ of the wavelength of the light used for sensing in the respective layer.

In one embodiment, the forming includes disposing alternately a high refractive index layer and a low refractive index layer. For example, the high and low refractive indices can have a difference of at least 0.1.

In one embodiment, the selecting includes selecting a refractive index ($n_l$), a thickness ($d_l$), and a reflectance ($r_l$) of the top layer such that they satisfy the following equations:

$$r'_s = \frac{r_s - r_l}{1 - r_s r_l} \text{ and } r_{net} = \frac{r_l + r'_s e^{-j2\phi_l}}{1 + r_l r'_s e^{-j2\phi_l}} = \pm j\beta$$

$$\frac{[r'_s(1+r_l^2)]^2 - [r_l(1+r'^2_s)]^2}{(1-r_l^2 r'^2_s)^2} = \beta^2$$

$$\cos\left(4\pi \frac{n_l d_l}{\lambda}\right) = -\left(\frac{r_l}{r'_s}\right)\left(\frac{1+r'^2_s}{1+r_l^2}\right)$$

wherein $\beta$ is an amplitude of a total reflectance coefficient $r_{net}$ of the stack including the top layer, wherein the total reflectance coefficient is imaginary and has a form of $\pm j\beta$, wherein j is the imaginary unit and $\pm j=\sqrt{-1}$, and $r_s$ and $r_s'$ are the reflectance of the substrate and the plurality of bi-layers combined, calculated with air and the top layer as the ambient medium, respectively, and wherein $\lambda$ is the wavelength of the light used for imaging or sensing.

In one embodiment, the forming an array of a plurality of stacks each having a substantially imaginary reflectance.

In one embodiment, the materials are selected to be substantially free of inorganic semiconductor or semiconductor oxide. In one example, the materials are selected to consist essentially of polymers.

In one embodiment, the materials are selected such that the stack has a purely imaginary reflectance.

In one embodiment, the materials are selected such that the stack is configured to have an optimal signal-to-noise ratio in a reflected signal.

In one embodiment, the materials are selected such that the plurality of thin films each have a purely real refractive index. In one example, the materials include polycarbonate and poly (methyl methacrylate).

In one embodiment, the forming includes disposing the plurality of thin films alternately with high refractive index values and low refractive index values, and wherein a difference between the high refractive index and the low refractive index is at least 0.1.

In another aspect, a method is provided for sensing or imaging a sample. The method includes providing a stack comprising a plurality of thin films, wherein the stack has a substantially imaginary total reflectance for light at a wavelength λ used for imaging or sensing. The method further includes directing a beam of light toward the stack in the absence of the sample, measuring the reflectance of the stack in the absence of the sample, disposing a sample over the stack, measuring the reflectance of the stack in the presence of the sample, and obtaining the difference in reflectance of the stack in the presence and absence of the sample.

In one embodiment, the plurality of thin films comprise polymer thin films. The plurality of thin films can include a plurality of bi-layers, wherein each of the plurality of bi-layers comprises a layer of high refractive index and a layer of low refractive index. In one embodiment, the layer of high refractive index and the layer of low refractive index each have a thickness of approximately ¼ of the wavelength λ, of the light used for imaging or sensing in the respective layer.

In one embodiment, the stack has a purely imaginary reflectance. The light can include one of a millimeter wave, an infrared, an optical, or an ultraviolet radiation.

In one embodiment, the method further includes disposing a plurality of samples over an array of a plurality of stacks each having a substantially imaginary reflectance. In one example, the sample comprises at least one of a drug, a chemical, or a biological agent.

In one embodiment, the directing a beam includes scanning a surface of the stack including the sample with the beam.

In one embodiment, the method further includes optimizing a signal-to-noise ratio in a reflected signal from the stack by selecting a structure of the stack.

In one embodiment, the directing of a beam includes directing a laser beam to illuminate a sample to be sensed, and detecting the reflected laser beam with a photodetector.

In one embodiment, the method further includes disposing the sample and the stack in a medium, wherein the directing is performed by directing the beam toward the sample through the medium.

In one embodiment, the medium comprises an analyte, wherein the sample is a biological sample, the method further comprising forming a biological or chemical reaction between the biological sample and the analyte.

Various embodiments may include any of the above elements or steps, alone or in any suitable combination.

As used herein the term "light" is to be understood to include electromagnetic radiation both within and outside of the visible spectrum, including, for example, ultraviolet and infrared radiation.

As used herein, the term "real reflectance" means the generally complex reflectance having only a real component. The term "imaginary reflectance" means the generally complex reflectance having only an imaginary component. The term "arbitrary reflectance" means any value between 0 and 1 for the magnitude of the reflectance.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 3(a) is plotted for noise parameters (Eq. 9)=$\alpha_{RIN}$=$\alpha_s$=0. FIG. 3(b) is for $\alpha_{RIN}$=100, and $\alpha_s$=10.

DETAILED DESCRIPTION

Figure 1:
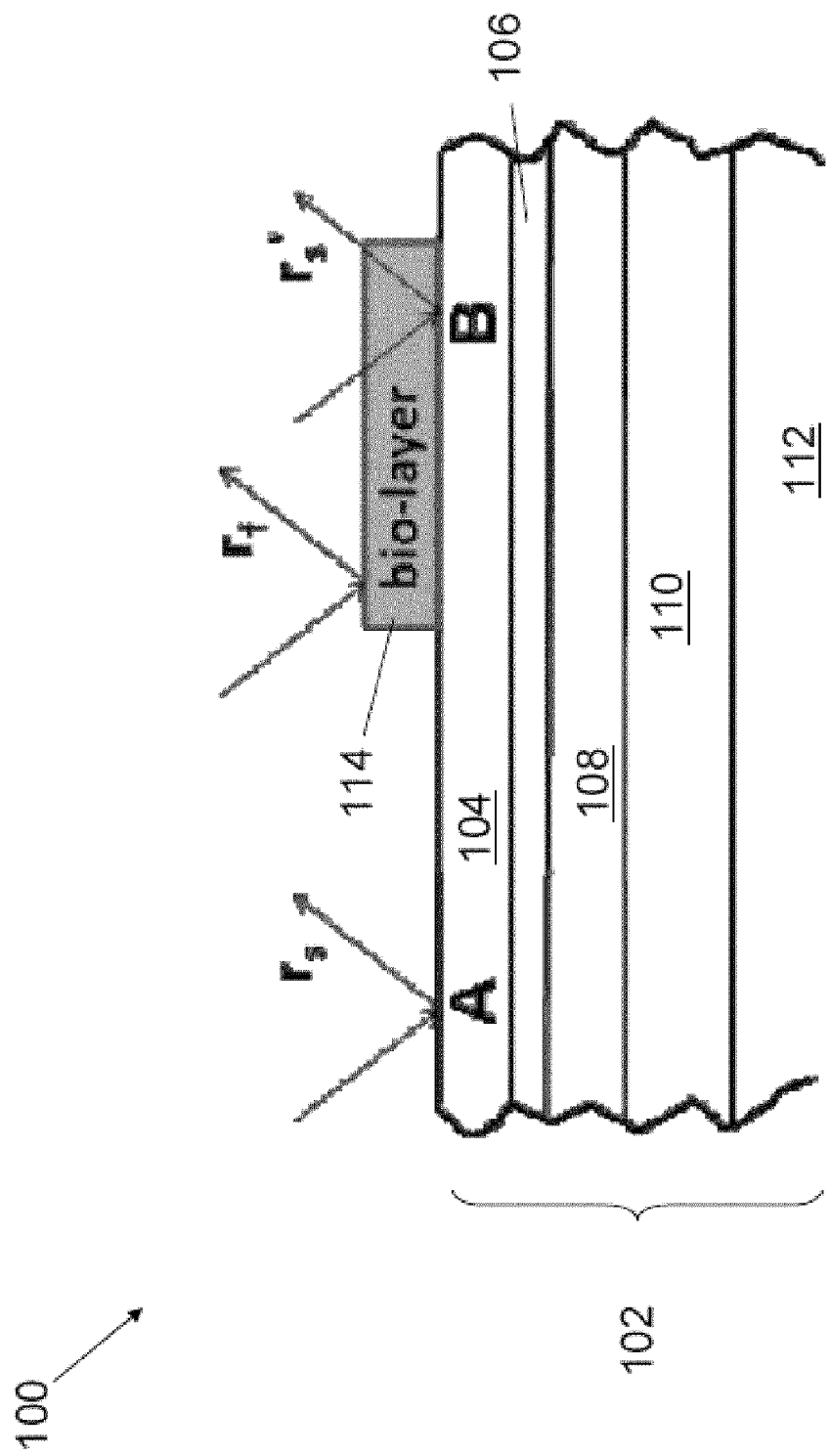
FIG. 1 is a schematic diagram illustrating a stacked thin film structure over which a bio-molecular layer is disposed. The biological layer can cause the reflectance of the structure to change locally. This is used in accordance with one embodiment to sense or image the bio-molecular layer.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein. Methods, apparatus, systems, and devices related to sensors and imagers are described. For example, low-cost sensors are provided, which are useful for example for sensing or imaging analytes such as biological samples.

Reflectance changes due to the presence or binding of molecules on thin-film stack structures is exploited for analyte sensing in accordance with an embodiment disclosed herein. The signal to noise ratio (SNR) for sensing or imaging is improved by selecting the thin film materials and by designing the stack structure. The noise floor of the sensors in accordance with embodiments disclosed herein can be in the range of 1-10 pm, matching the performance of Surface Plasmon Resonance (SPR) based sensors. Sensitive, low-cost, easy-to-fabricate, large-area sensors with high multiplexing capabilities are developed.

A method is provided for fabricating the improved stacks using low-cost materials, such as polymers, such as polycarbonate. Such materials are less expensive compared with conventional semiconductor and dielectric materials, and can have simpler fabrication processes.

Different interrogation schemes such as intensity measurement at a fixed wavelength, and measurement of the reflectance spectra can be employed. The magnitude of reflectance changes resulting from a unit bio-molecular layer can be measured. The thin film stack can be designed to maximize the reflectance contrast for the unit analyte layer.

As described in detail below, in accordance with one embodiment, the reflectance change due to an analyte layer on a thin film stack is derived as a function of stack's complex reflectance coefficient. A thin film stack with a purely imaginary reflectance coefficient can maximize the SNR of molecular sensing, irrespective of the system noise being dominated by intensity-dependent terms (RIN and shot noise) or intensity-independent terms (electronic noise, dark noise). Subsequently, a thin film stack structure capable of producing an arbitrary purely imaginary reflectance coefficient using typical refractive index values of common polymer materials (i.e., purely real refractive indices) is provided.

FIG. 1 is a cross-sectional view of an apparatus 100 for sensing or imaging. The apparatus 100 includes a stack 102. In one embodiment, the stack 102 includes a plurality of thin films, for example, at least four layers of thin films. In the embodiment shown in FIG. 1, the stack 102 includes a plurality of thin films 104, 106, 108, 110, 112. The thin films can include, for example, organic thin films, polymer thin films, etc. In one embodiment, the stack consists essentially of organic materials. In one embodiment, the stack consists essentially of polymers. In one example, the stack contains substantially no inorganic semiconductor or semiconductor oxide.

The apparatus 100 is configured to sense or image a sample 114 disposed over the stack 102, through a change in reflectance caused by the sample 114.

In one embodiment, the stack 102 is designed to have a substantially imaginary total reflectance coefficient. To achieve such a reflectance, inorganic dielectric films such as $SiO_2$, $TiO_2$, $Ta_2O_5$, or organic or inorganic polymer thin films can be used. On the other hand, doped silicon cannot achieve an arbitrary purely imaginary reflectance because its material reflectance coefficient is fixed.

The manufacturing process may cause a thickness variation of the layers in the stack. The variation can be, for example, less than 5%, e.g., in the range of 1-5%. In some such case, the ratio of the real part to the imaginary part of the reflectance (in other words the "impurity" of the reflectance) will be 2-3% which is acceptable based on the SNR considerations. For typical applications, this wavelength variation is acceptable because it is possible to get less than 0.1% spectral purity using commercially available filters. The purity of the spectrum may be further improved using narrow band light sources such as lasers.

In general, the purity of the imaginary reflectance of the stack may be determined using standard ellipsometric techniques know in the art. For example, for a stack designed to for use with interrogation light at an operational wavelength $\lambda$, a single wavelength ellipsometric measurement may be performed at the operational wavelength $\lambda$ to determine the ratio of the real part to the imaginary part of the reflectance. In some such cases, the real part may be less than 5% of the imaginary part, less than 4% of the imaginary part, less than 3% of the imaginary part, less than 2% of the imaginary part, less than 15 of the imaginary part, etc., e.g., in the range of 2-3% of the imaginary part.

For a stack designed to for use with interrogation light at a spectral range of operational wavelengths, a multiple wavelength ellipsometric measurement may be performed over the spectral range to determine maximum the ratio of the real part to the imaginary part of the reflectance over the spectral range. In some such cases, for the maximum ratio, the real part may be less than 5% of the imaginary part, less than 4% of the imaginary part, less than 3% of the imaginary part, less than 2% of the imaginary part, less than 15 of the imaginary part, etc., e.g., in the range of 2-3% of the imaginary part.

The stack 102 can be designed to achieve a purely imaginary reflectance with an arbitrary magnitude, for example, in the form of $\pm j\beta$, using materials having purely real refractive indices (e.g., polymers). In one embodiment, the polymers do not have any absorption in the visible wavelength range used for sensing or imaging. Therefore, their refractive indices can be perfectly pure.

Figure 2:
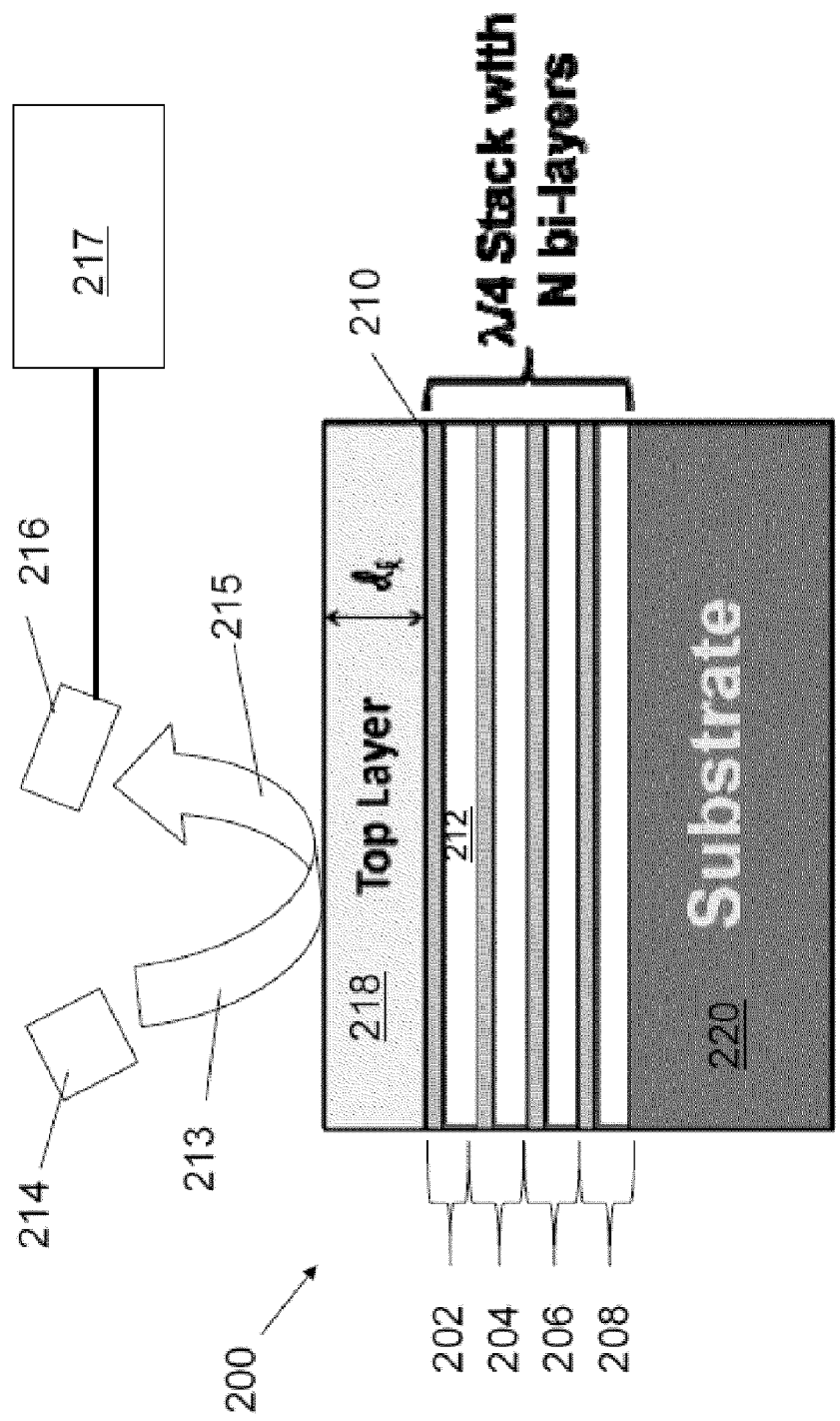
FIG. 2 is a cross-sectional view of a thin film structure in accordance with one representative embodiment, which can realize an arbitrary reflectance of the type $\pm j\beta$.

With reference to FIG. 2, the sensing or imaging apparatus 200 includes a plurality of bi-layers 202, 204, 206, 208. For example, the bi-layer 202 comprises a layer 210 of high refractive index and a layer 212 of low refractive index. The high refractive index can be, for example, in the range of 1.45-1.65, and the low refractive index is lower than the high refractive index. In one embodiment, the difference between the high and low refractive indices is at least 0.1.

In one non-limiting example, the layer 210 has a refractive index of about 1.6, and the layer 212 has a refractive index of about 1.5. The layer of high refractive index and the layer of low refractive index each have a thickness of approximately ¼ of a wavelength of an electromagnetic (EM) radiation in the respective layers. For example, when a 1 μm infrared (IR) EM radiation is used for sensing or imaging, the layer 210 has a thickness of about 1 μm/1.6/4=0.156 μm, and the layer 212 has a thickness of about 1 μm/1.5/4=0.167 μm.

In some other examples, the EM radiation comprises one of a millimeter wave, an optical, an infrared, or an ultraviolet radiation for sensing or imaging. The apparatus 200 can further include a light source, such as a laser 214, configured to emit the EM radiation 213 toward a sample to be sensed or imaged. A photodetector 216, such as a photodiode, is configured to receive reflected EM radiation 215. The photodetector 216 can be coupled to a processor or computer 217, which analyzes the measured data to obtain the reflectance and eventually the properties of the sample.

Various types of analytes can be analyzed using the methods and apparatuses disclosed herein. These analytes can be biological or non-biological analytes. For example, the analyte can be a chemical sample, and the apparatus is configured as a chemical sensor. Examples of non-biological samples may include adsorbed gases (e.g., ethanol vapors, methane etc.), contaminating ions in drinking water or food such as fluorides or nitrates. The analyte can be a drug, and the apparatus can be used to analyze the type and composition of the drug. The analyte can be biological fluids, and the apparatus is configured as a biosensor. Biological fluids include, but are not limited to, e.g., aqueous humour and vitreous humour; whole blood; blood serum; breast milk; cerebrospinal fluid; cerumen (earwax); endolymph and perilymph; gastric juice; mucus (including nasal drainage and phlegm); peritoneal fluid; pleural fluid; saliva; sebum (skin oil); semen; sweat; tears; vaginal secretion; vomit; and urine.

The analyte can also be an optical material, and the apparatus can be used to measure, for example, color characteristics of the optical material using incident light of various wavelengths. That is, the apparatus measures "optical" perturbations, which include "refractive index perturbations," caused by the presence of the sample, and "thickness perturbations," e.g., caused by polymer layers swelling in certain solvents etc. The color characteristics of the optical material can be considered as a refractive index perturbation, and can be detected using this approach.

The stack further includes a top layer 218 and a substrate 220. When polymer thin films are adopted, for any given choices of polymers, by changing the number of bi-layers one can change the effective reflectance coefficient of the substrate and the top layer by designing the thicknesses of these layers. These thicknesses can be mathematically calculated to ensure that a purely imaginary net reflectance is obtained.

The substrate can be disposable. In one embodiment, the substrate comprises one of glass, polycarbonate, or polystyrene. In one embodiment, the top layer comprises poly (methyl methacrylate).

Using the transfer matrix method known in the art, the stack as illustrated in FIG. 1 or FIG. 2 can be represented by a net reflectance coefficient $r_s$ at point A, which is the total reflectance coefficient of the stack including the substrate. The net reflectance coefficient $r_s$ can be modified to become $r_s'$ at point B when an analyte sample 114 is disposed over the stack 102. The analyte sample 114 can be, for example, a bio-molecular layer comprising a monolayer of biological molecules such as DNA or proteins. Receptors for various target molecules, e.g., antibodies for disease markers, can be attached to the thin film stack. Binding of the target molecules to the receptor can change the reflectance of the stack.

In one embodiment, the EM radiation beam at an operational wavelength λ (e.g., the wavelength in the air) from a light source scans the top surface of the stack 102. A net reflectance coefficient of $r_s$ can be obtained at point A and at locations where there is no sample. A modified reflection coefficient $r_s'$ can be obtained at point B where the sample 114 is present. The ambient medium can be vacuum or air (n=1), or other media with an n≠1. The sample layer 114 can have its refractive index, thickness, and reflectance denoted by $n_f$, $d_f$, and $r_f$, respectively. The net reflectance coefficients at points A and B are:

$$r_A = r_s \text{ and } r_B = \frac{r_f + r_s' e^{-j2\phi_f}}{1 + r_f r_s' e^{-j2\phi_f}}; \phi_f = 2\pi \frac{n_f d_f}{\lambda}. \quad (1)$$

The sample 114 can have a purely real refractive index, e.g., $n_f$~1.3-1.5, and consequently a purely real Fresnel reflection coefficient $r_f$ when the ambient medium also has a real refractive index. At point B, the stack 102 can be considered as having the sample layer 114, instead of air, as the ambient medium. The $r_s'$ can then be calculated using the matrix formalism. The reflected and transmitted electric fields from a thin film stack can be modeled as a single matrix M as:

$$M = D_a^{-1} \left[ \prod_{i=1}^{N} D_i P_i D_i^{-1} \right] D_s. \quad (2)$$

Here the subscripts "a" and "s" represent the ambient medium and the substrate, respectively. The matrix $D_i$ for any i can be written as:

$$D_i = \begin{pmatrix} 1 & 1 \\ n_i \cos\theta_i & -n_i \cos\theta_i \end{pmatrix} \text{ and for TE polarization,} \quad (3a)$$

and $$D_i = \begin{pmatrix} \cos\theta_i & \cos\theta_i \\ n_i & -n_i \end{pmatrix} \text{ for TM polarization} \quad (3b)$$

$$P_i = \begin{pmatrix} e^{j\phi_i} & 0 \\ 0 & e^{-j\phi_i} \end{pmatrix}; \phi_i = 4\pi \frac{n_i d_i}{\lambda}. \quad (3c)$$

Using Equation (3), it can be shown that when the ambient medium changes from air to the sample layer 114, as for points A and B, respectively, in FIG. 1, the reflectance of the stack 102 for either polarization gets modified to:

$$r_s' = \frac{r_s - r_f}{1 - r_s r_f}. \quad (4)$$

Substituting Eq. (4) in (1), $r_B$ gets modified as:

$$r_B = \frac{(e^{j\phi_f} - e^{-j\phi_f})r_f - (r_f^2 e^{j\phi_f} - e^{-j\phi_f})r_s}{(e^{j\phi_f} - r_f^2 e^{-j\phi_f}) - (e^{j\phi_f} - e^{-j\phi_f})r_s r_f}. \quad (5)$$

Equation (5) can be simplified by noting that typical values of $n_f$ and $d_f$ are 1.3-1.5, and 2-3 nm, respectively, implying $\phi_f \ll 1$, and $r_f \approx 0.15$. Therefore, collecting only linear terms in $\phi_f$ and $r_f$, Eq. (5) can be rewritten as $$r_B = r_s + j2\phi_f(r_s^2 r_f - (r_s - r_f)) \quad (6)$$

Note that $r_f$ is purely real whereas $r_s$ in general has a complex value. The reflectance difference ΔR with and without the sample layer 114 is then:

$$\Delta R = |r_B|^2 - |r_A|^2 = 4\phi_f r_f(1 - |r_s|^2) Im(r_s) \quad (7)$$

Equation (7) provides a design guideline for constructing thin-film, reflectance-based sensors or imagers. Specifically, thin-film structures that have a purely real reflectance coefficient or are perfectly reflecting do not produce any reflectance contrast, as can be seen from Eq. (7).

To find out the value of $r_s$ that maximizes the reflectance contrast, one cannot simply maximize the expression in Eq. (7). Rather, the stack is should be designed to have an optimal SNR. This is because noise in optical systems can have intensity-dependent components which may dominate the total noise. Generally one can write the total noise per bandwidth as, $$\sigma_{tot}^2 = \sigma_{RIN}^2 I^2 + \sigma_s I + N_o^2 \quad (8)$$

Here $\sigma_{RIN}$ is the relative intensity noise coefficient, $\sigma_s$ is the shot noise coefficient, $N_o$ is the back ground noise, e.g., from the detector electronics, and I is the mean intensity of the detected light reflected from the stack. For a typical laser diode, $\sigma_{RIN} \approx 10^{-3}$-$10^{-2}$, and is the dominant intensity-dependent noise term. Shot noise typically dominates only at low incident power levels.

The SNR can then be written as:

$$SNR = \frac{P_o \Delta R}{N_o (1 + (\alpha_{RIN} P_o R_s)^2 + \alpha_s P_o R_s)^{1/2}}, \quad (9)$$

where $\alpha_{RIN}=\sigma_{RIN}/N_o$, $\alpha_s=\sigma_s/N_o$, $P_o$ is the incident laser power, $R_s$ is the amplitude reflectance of the thin film structure, and $\Delta R$ is from Eq. 7.

It can be shown that SNR given by Eq. (9) is maximized by $r_s=\pm j\beta$, for any $\alpha_{RIN}$ or $\alpha_s$. The value of $\beta$ depends on the operating noise regime (e.g., the values of $\alpha_{RIN}$ and $\alpha_s$). In one example, when $\alpha_{RIN}=\alpha_s=0$, SNR given by Eq. 9 is maximized when $r_s=\pm j/\sqrt{3}$.

Figure 3:
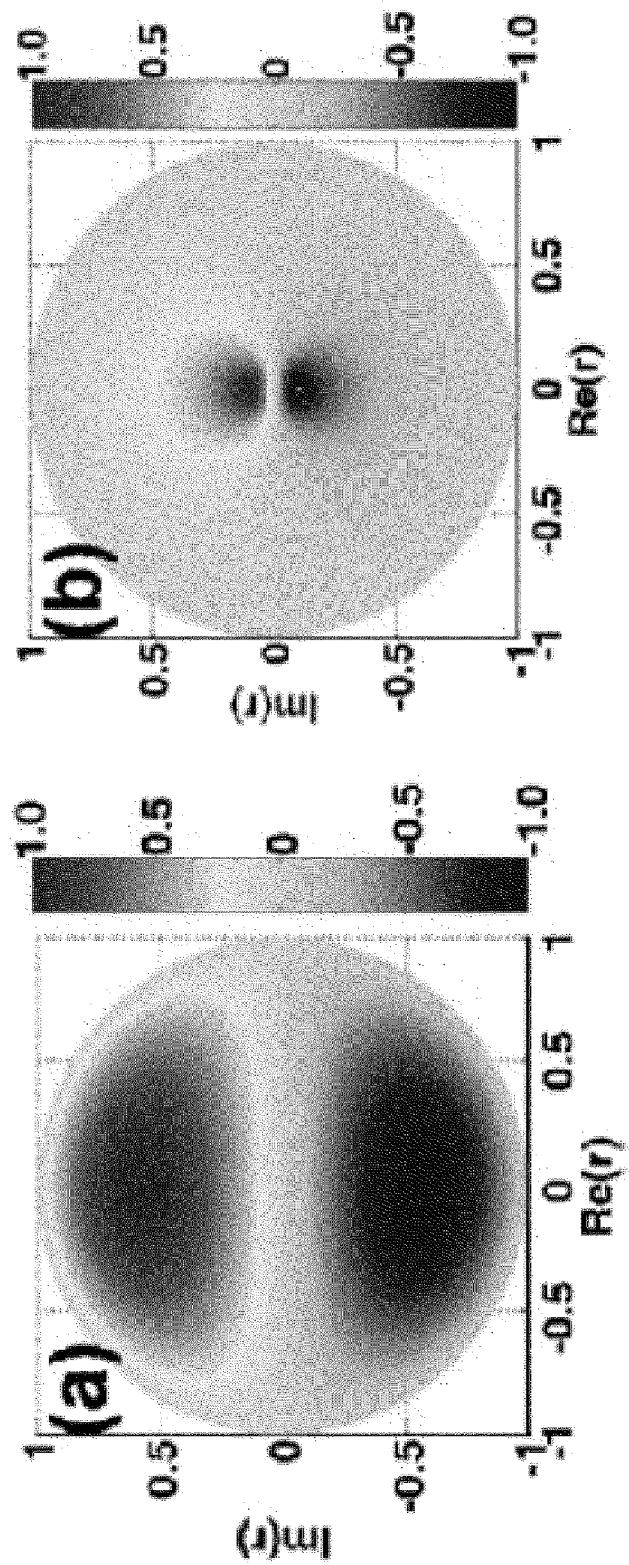
FIG. 3 illustrates signal-to-noise ratio (SNR) of reflectance from an example bio-molecular sensor as a function of real and imaginary components of the substrate reflectance coefficient under various noise regimes given by Eq. (9) described below. The substrate reflectance having the form of $\pm j\beta$ with $\beta$ dependent on noise regime maximizes the SNR.

FIG. 3 shows normalized SNR as a function of the real and imaginary parts of the substrate reflectance for (a) $\alpha_{RIN}=\alpha_s=0$, and (b) CT $\alpha_m=100$ and $\alpha_s=10$.

The performance measure derived in Eq. (9) is merely illustrative. In some molecular sensing system, other noise sources may exist, such as non-specific binding of molecules, interference from competing molecular species in complex samples, etc. Similar issues to any other sensor systems, and are not specific to sensors and imagers disclosed herein. Thus, analyses of these effects in the performance are not presented here.

For the structure shown in FIG. 2, $n_l$, $d_l$, and $r_l$ represent the refractive index, thickness, and reflectance, respectively of the top layer, and $r_{net}$ represents the net reflectance of the structure (substrate+stack+top layer). From Eq. (1) and Eq. (4), it can be obtained that $$r'_s = \frac{r_s - r_l}{1 - r_s r_l} \text{ and } r_{net} = \frac{r_l + r'_s e^{-j2\phi_l}}{1 + r_l r'_s e^{-j2\phi_l}} = \pm j\beta. \tag{10}$$

Solving Eq. (10) leads to:

$$\frac{[r'_s(1+r_l^2)]^2 - [r_l(1+r'^2_s)]^2}{(1-r_l^2 r'^2_s)^2} = \beta^2 \tag{11a}$$

$$\cos\left(4\pi\frac{n_l d_l}{\lambda}\right) = -\left(\frac{r_l}{r'_s}\right)\left(\frac{1+r'^2_s}{1+r_l^2}\right). \tag{11b}$$

Eqs. 11(a) and 11(b) can be used as design criteria for the thin film structures. For example, a polymer material (e.g., $n_l=1.5$) is selected as the top layer, thus fixing $r_l$. Then Eq. (10) gives the appropriate value of $r_s$. The reflectance $r_s$ of the alternating high and low index quarter-wave thin film stack depends on the stack length, asymptotically reaching unity with increasing length. Therefore, for a given $r_s$, one can find the desired stack length for a given combination of high and low index polymers. Once $r_s$ is fixed, Eq. (11b) gives the appropriate thickness of the top layer.

By interchanging the order of the stack, the sign of the net reflectance can be reversed, e.g., from + to −, indicating a polarization angle change of the reflected light.

Figure 8:
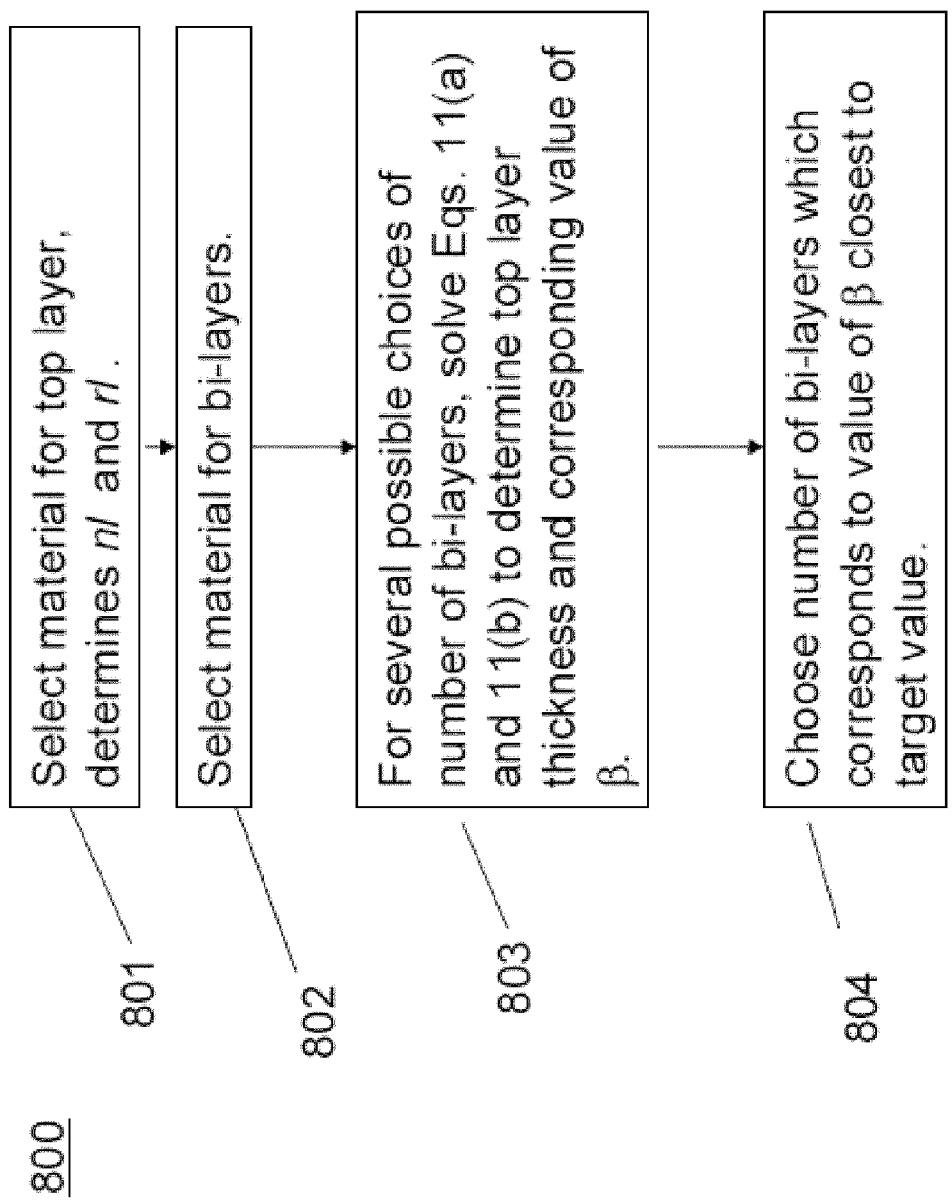
FIG. 8 shows a non-limiting example of a method for designing a stack structure of the type shown in FIG. 1.

FIG. 8 shows a non-limiting example of a method 800 for designing a stack structure of the type shown in FIG. 1 with a target value of imaginary reflectance, based on Eqs. 11(a) and 11(b) above. In step 801, the material of the top layer 218 is selected, thereby determining the index of refraction and reflectance $n_l$, and $r_l$ of the layer.

In step 802, the material s of the bi-layers in the bi-layer quarter wave stack 212 are selected, fixing the index of refraction of the layers.

For each bi-layer, the layer of high refractive index and the layer of low refractive index each have a thickness of approximately ¼ of a wavelength $\lambda$ the interrogation light used with the sensor. Accordingly, the overall thickness of the stack of bi-layers may be determined for any choice for the number of bi-layers in the stack.

In step 803, several possible choices of the number of bi-layers in the stack (e.g., a range of 2-20 bi-layers, 3-20 bi layers, 4-20, bilayers, 5-20 bi-layers, 6-20 bi layers, or any other suitable choice) are set out. For each of these possible choices, Eqs. 11(a) and 11(b) are solved to determine the thickness of the top layer $d_l$. For each possible choice of the number of bi-layers, the solution of Eqs. 11(a) and 11(b) will yield a corresponding value of the imaginary reflectance $\beta$.

In step 804, the possible choice of the number of bi-layers in the stack having a corresponding value of $\beta$ closest to the target value is selected. Accordingly, the structure of the stack is fully determined.

The following Table 1 provides some examples of the materials and structures of stacks determined using the design method described above. Most of the polymers have refractive indices in a range 1.45-1.65. In these combinations of polymers, a polycarbonate (PC) is used as the substrate because it is readily available. Polystyrene (PS) or poly (methyl methacrylate) (PMMA) are used as the top layer, and are suitable for attaching DNA and proteins for diagnostic sensing. However, it is noted that many other materials can be used. In the "Polymer Combination," "n" represents the number of bi-layers. The range of purely imaginary reflectance depends on the number of bi-layers, where the higher number of bi-layers confers a higher purely imaginary reflectance value.

In the following table, CA represents cellulose acetate, PVA represents poly-vinyl alcohol, PAA represents poly-acrylic acid, and MC represents methyl cellulose.

TABLE 1

Stack structures on polycarbonate substrates

| | Polymer Combination (bi-layer) | High n polymer, thickness (nm) | Low n polymer, thickness (nm) | Number of bi-layers | Top layer, thickness (nm) | Range of purely imaginary reflectance |
|---|---|---|---|---|---|---|
| 1 | (CA-PAA) | PAA, 103 nm | CA, 107 nm | 5-20 | PMMA, 68 nm | 0.11-0.67 |
| 2 | (CA-PAA) | PAA, 103 nm | CA, 107 nm | 6-20 | PS, 63 nm | 0.05-0.63 |
| 3 | (PMMA-PS) | PMMA, 107 nm | PS, 99 nm | 3-20 | PS, 66 nm | 0.17-0.92 |
| 4 | (MC-PVA) | MC, 108 nm | PVA, 102 nm | 4-20 | PMMA, 66 nm | 0.13-0.78 |
| 5 | (PVA-PS) | PVA, 102 nm | PS, 99 nm | 3-20 | PMMA, 66 nm | 0.05-0.82 |

In Table 1, referring to row 1, the polymer combination of (CA-PAA)n-PMMA for example, PMMA is selected for the top layer material. Thus, $n_l$ is selected to be 1.5, thus fixing $r_l$. The thickness and material for the bilayers are chosen, with each bilayer composed of 103 nm PAA and 107 nm CA, where the thicknesses are each ¼ of the wavelength of the light within each layer. Eqs. 11(a) and 11(b) are solved over a range of 5-20 bilayers, giving a top layer thickness of 68 nm, and a range of corresponding $\beta$ values running from 0.11 (for 5 bi-layers) to 0.67 (for 20 bi-layers). If the desired target value of β is 0.1, 5 bi-layers would be chosen for the stack design. The resulting structure, (CA-PAA)5-PMMA over a PC substrate, would have a purely imaginary reflectance coefficient with the desired value β.

The target value of β is selected based on whether a high or low reflectance is needed for the measurements. For example, the value of β is chosen based on the noise distribution of the system. In one example, depending on factors such as cost, certain light source, photodetector and related electronics may be selected. This selected system will have certain noise characteristics, e.g., the noise may be dominated by the electronics, and an example β value of about 0.58 can result in optimal SNR. In some selected systems, the noise may be dominated by the light source. Depending on the ratio of the light source noise to the electronic noise, the optimal value of β can be calculated by maximizing the SNR equation. Once β is determined, the optimal sensor chip for the given detection system can be designed following the steps described herein.

Figure 4:
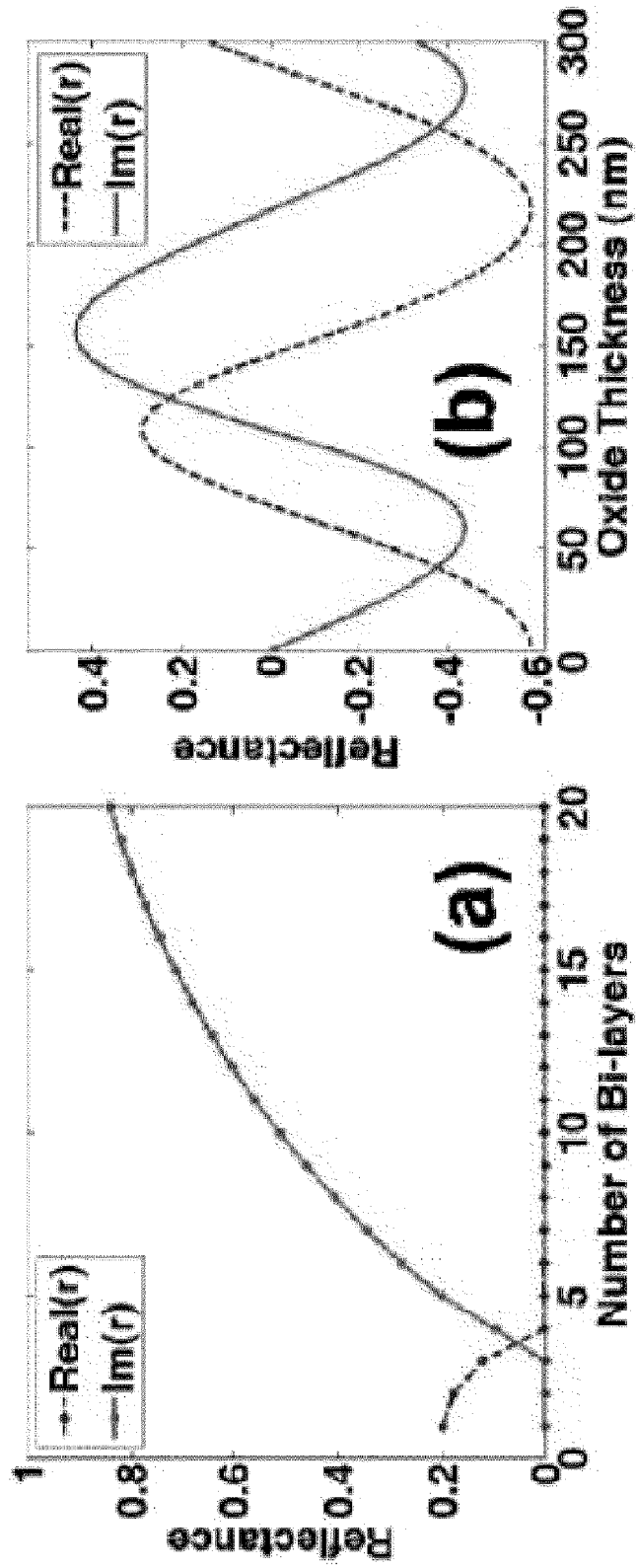
FIG. 4 illustrates the real (dashed line) and imaginary (solid line) components of the reflectance coefficients of: (a) the thin film stack illustrated in FIG. 2; and (b) a $Si/SiO_2$ structure. Unlike the $Si/SiO_2$ structure, the thin film stack illustrated in FIG. 2 can produce an arbitrary reflectance of the type $\pm j\beta$. The Length of stack refers to the number of high and low refractive index bi-layers.

FIG. 4(a) shows the real and imaginary reflectance coefficients of a multilayer stack structure using a polycarbonate substrate (n=1.6), a top layer of n=1.5 (e.g., PMMA), low and high refractive indices of n=1.5 and 1.6, respectively. The design parameters are obtained from Eqs. 11(a) and 11(b). The designed stack structure is capable of creating any arbitrary (limited by the discreteness of stack length) reflectance of the type ±jβ for normal incidence. In contrast, as illustrated in FIG. 4(b), a conventional $Si/SiO_2$ structure can only achieve approximately purely imaginary reflectance for only a few fixed oxide thicknesses.

Figure 5:
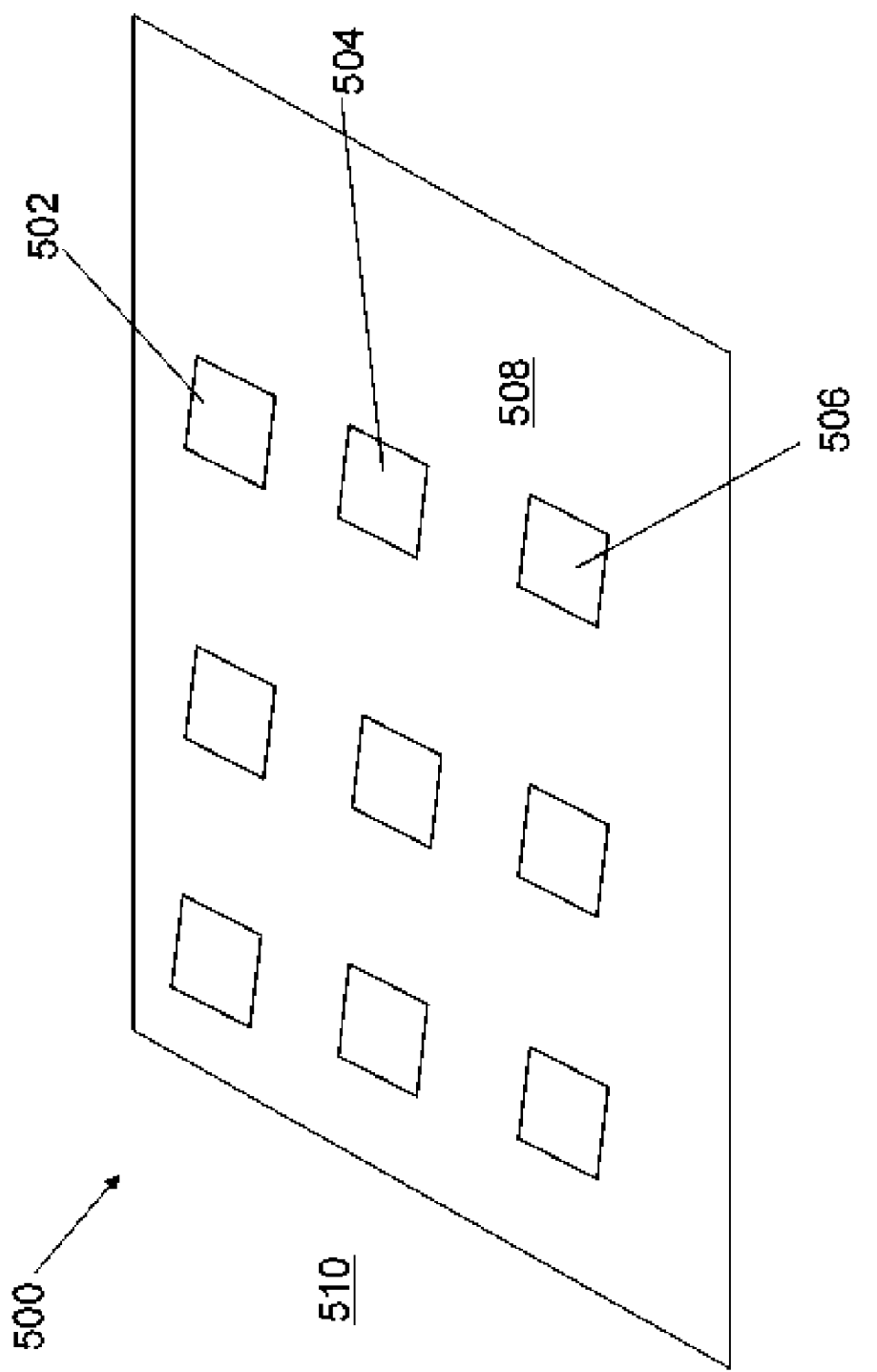
FIG. 5 is a schematic diagram illustrating an embodiment of the sensing or imaging apparatus including an array of a plurality of stacked thin-film structures for sensing or imaging a plurality of samples.

In one embodiment, with reference to FIG. 5, a sensing or imaging apparatus 500 comprises an array of a plurality of stacks 502, 504, 506, . . . , disposed over a substrate 508. Each of the plurality of stacks 502, 504, 506 has a substantially imaginary reflectance. The SNR of the reflected light signal can be optimized by designing the structure of the stacks as described above. The apparatus 500 is configured to sense a plurality of samples. The plurality of samples can be disposed over the array, for example, using a robotic arm.

A light source such as a laser beam can be directed to scan across the array of stacks and the plurality of samples. Alternatively, a flood light, or a plurality of light sources can be used. The reflected light signals can be detected with one or more photodetectors.

In some embodiments, the samples and the array of stacks can be disposed in a medium 510, and the laser beam can be directed toward the samples and the array through the medium 510. The medium can comprise, for example, an analyte. The samples can be biological samples, and can have biological or chemical reactions with the analyte. The biological samples may include, for example, serum, cell extracts containing specific proteins of interest or DNA sequences of interest, cereberospinal fluid, etc.

Figure 6:
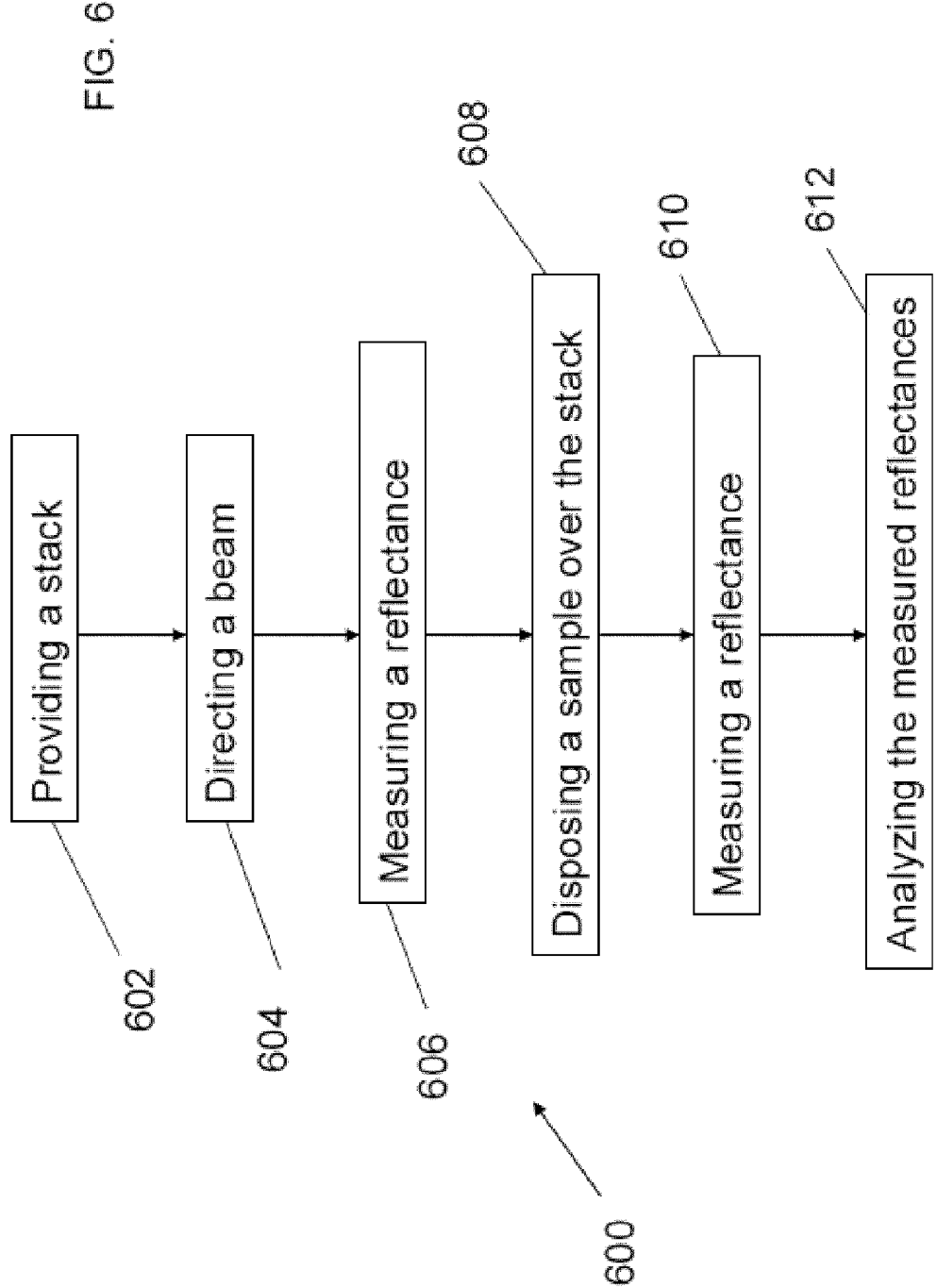
FIG. 6 is a flowchart illustrating a method of sensing or imaging in accordance with one embodiment.

Based on the above, with reference to FIGS. 1, 2, and 6, a method 600 of sensing or imaging a sample 114 is provided. The method 600 includes, for example, in step 602, providing a stack 102 comprising a plurality of thin films 104, 106, 108, . . . , wherein the stack 102 has a substantially imaginary total reflectance. The method 600 further includes, in step 604, directing a beam 213 of EM radiation toward the stack in the absence of a sample, and in step 606, measuring the reflectance of the stack in the absence of the sample. In step 608, a sample 114 is disposed over the stack, and the reflectance of the stack is measured in step 610 in the presence of the sample 114. In step 612, the measured reflectances are analyzed, and the difference in reflectance of the stack in the presence and absence of the sample can then be obtained.

The stacks in accordance with embodiments disclosed herein can be used to create optimal conditions for analyte sensing or imaging under any operating noise regime, and can achieve similar or better sensing performance compared with the conventional $Si/SiO_2$ sensors.

Figure 7:
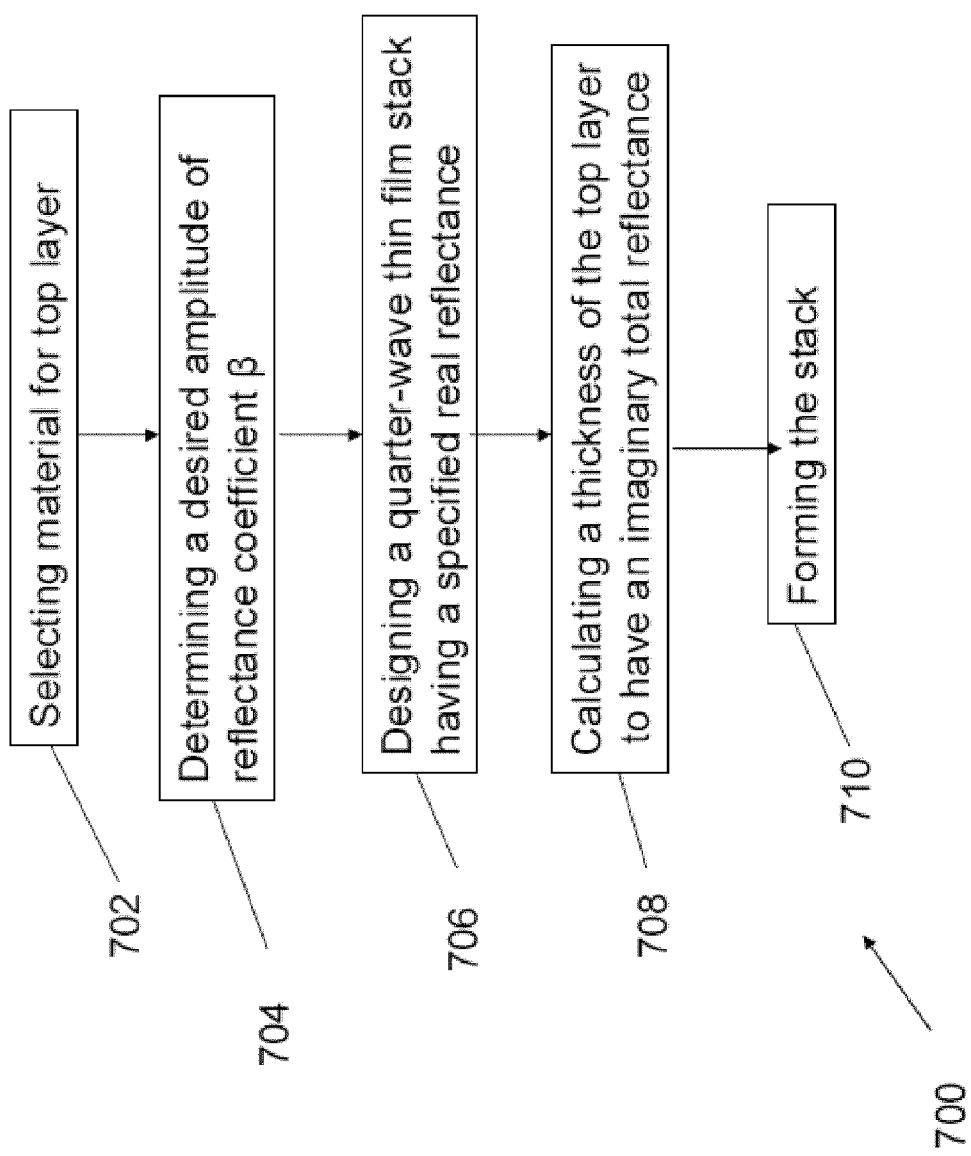
FIG. 7 is a flowchart illustrating a method of making a sensor or imager in accordance with one embodiment.

Scattering due to roughness, long-range uniformity, and chemical stability of the polymer layers may be factors in the designs, but can be managed in the fabrication process. Referring to FIG. 7, a method 700 of making a sensor or imager is provided.

In one embodiment, the method includes, in step 702, selecting materials for a top layer. In step 704, a desired amplitude of reflectance coefficient β is determined. In step 706, a quarter-wave thin film stack comprising a plurality of bi-layers is designed to have a specified real reflectance. In step 708, the thickness of the top layer is calculated. The stack structure is thus designed, through the selection of materials and designing the layer thicknesses, to have a substantially imaginary total reflectance. In one example, the materials are selected to be substantially free of inorganic semiconductor or semiconductor oxide. For example, the materials are selected to consist essentially of polymers. In step 710, the stack with the top layer, the plurality of thin films, and the substrate are formed.

Polymer thin film materials can be assembled via several low cost manufacturing processes such as spin coating, electrostatic layer-by-layer self assembly (LbL), inkjet printing, extrusion, or screen printing. The fabrication of such stacks on polystyrene substrate can employ electrostatic LbL of polyelectrolytes, which can be used to coat virtually any substrate, and have previously been used to create anti-reflection coatings. Low-cost substrates such as polycarbonate (PC) or even overhead transparency sheets can be used.

The radiation source such as the laser diode, and photodetectors add the cost to the sensing/imaging system. However, the cost associated with these components is much less than the cost of consumables such as the substrates and reagents, which determine the sensing/imaging cost in the long term. This situation is similar to that the cost of printing consumables such as cartridges far outweighs the cost of the printer itself. Thus, by making the substrates disposable, and selecting low-cost materials such as polymers for the stack, the cost is significantly reduced while retaining the performance of sensing/imaging as compared with conventional semiconductor sensors/imagers.

By using interferometric signals, at least one advantage of at least one embodiment disclosed herein includes reduced reagent consumption (e.g., there is no need for fluorescent labels etc.) and the subsequently reduced costs. The ability to screen samples using the "label-free" approach would also allow the sensors/imagers to have broader areas of applications compared with the screening methods that rely on fluorescent labels. These sensors and imagers for biological applications are also suitable to meet the demands of developing countries where the cost is important for widespread adoption of diagnostic chip technologies.

Polymer thin film materials are significantly cheaper than conventional semiconductor-grade materials. Conventional sensors based on semiconductor materials such as $SiO_2$ or $Si_3N_4$ on silicon substrates have attained good sensing performance, and these materials and associated fabrication resources such as clean rooms and e-beam thin film deposition systems may be easily accessible, but may require significant capital investment. As a result, the current cost of silicon is >$2800/m². In contrast, the current cost of glass slides is about $185/m², while the current cost of polycarbonate (PC) is about $19/m². Thus, the polymer thin film stack disclosed herein can have a cost of only about $\frac{1}{150}$ of the conventional silicon-based sensors. The low cost of glass slides of less than $200/m², and more so the PC of <$20/m² allows the substrate to be disposable.

As described above, the thin film stack structure can produce any arbitrary purely imaginary reflectance coefficient using materials (such as polymers) having purely real refractive indices. The reflectance change due to the presence of an analyte sample (e.g., bio-molecular) on a thin film stack as a function of a complex reflectance coefficient can be measured. The thin film stack with a purely imaginary reflectance coefficient maximizes the SNR of the molecular sensing/imaging process, irrespective of the system noise being dominated by intensity-dependent terms (RIN and shot noise) or intensity-independent terms (electronic noise, dark noise).

The sensors and imagers in accordance with embodiments disclosed herein can be configured as, for example, research laboratories biosensors, home diagnostic biosensors, low-cost home-based analytical/diagnostic test strips for various applications, point-of-care biosensors, process industry biosensors, environmental monitoring biosensors, pathogen sensors, and highly multiplexed bio-molecular sensors for the development of integrative or systems biology where a large number of genomic or proteomic variables must be quantified to infer their interdependences. Various diseases can be diagnosed through the detection of molecular markers of disease states.

The sample can be biological, or non biological. In some embodiments, the sample comprises a chemical material, and the apparatus is configured as a chemical sensor (e.g., for sensing the presence of volatile chemicals). In some other embodiments, the sample comprises a chemical material, and the apparatus is configured as a chemical sensor. In one example, the sample comprises a drug, and the apparatus is configured to perform analysis of the drug composition. In some embodiments, the apparatus is configured to sense or image a nano-scale thin film. The samples to be sensed or imaged can be non-absorptive.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor, printer, memory, etc. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

In general, the program outputs information. For example, the information can be output to another computer (e.g., over a network), written to memory, or output to a display or printer where a user can view the information.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim: and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

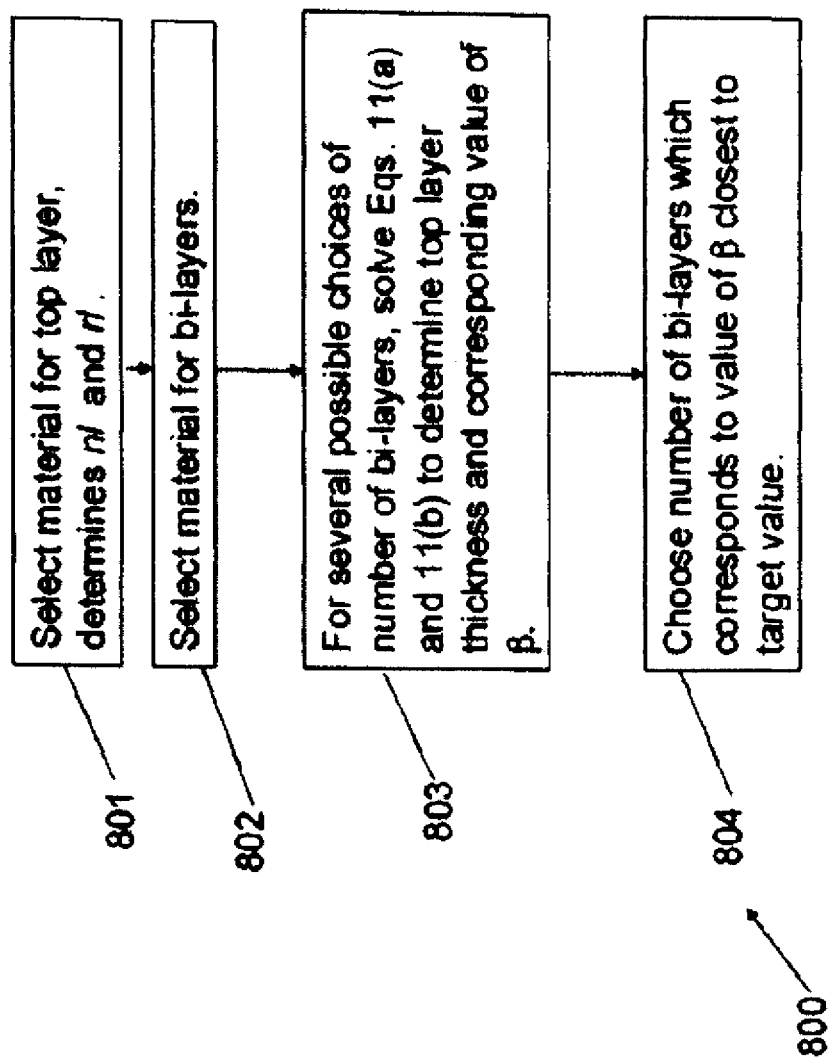

The invention claimed is:

1. An apparatus for sensing or imaging with light at a wavelength $\lambda$, the apparatus comprising:
    a stack including a plurality of thin films;
    wherein the stack has a substantially imaginary total reflectance coefficient for the light at the wavelength $\lambda$,
    wherein the substantially imaginary total reflectance coefficient is a total reflectance coefficient for which the real part of the reflectance is substantially zero, and the imaginary part of the reflectance is substantially non-zero.

2. The apparatus of claim 1, wherein the plurality of thin films comprise polymer thin films.

3. The apparatus of claim 1, wherein the plurality of thin films include a plurality of bi-layers, wherein each of the plurality of bi-layers comprises a layer of high refractive index and a layer of low refractive index.

4. The apparatus of claim 3, wherein the stack further includes:
    a top layer; and
    a substrate.

5. The apparatus of claim 4, wherein the top layer has a refractive index $(n_l)$, a thickness $(d_l)$, and a reflectance $(r_l)$ selected such that they satisfy the following equations:

$$r'_s = \frac{r_s - r_l}{1 - r_s r_l} \text{ and } r_{net} = \frac{r_l + r'_s e^{-j2\phi_l}}{1 + r_l r'_s e^{-j2\phi_l}} = \pm j\beta$$

$$\frac{[r'_s(1 + r_l^2)]^2 - [r_l(1 + r'^2_s)]^2}{(1 - r_l^2 r'^2_s)^2} = \beta^2$$

$$\cos\left(4\pi \frac{n_l d_l}{\lambda}\right) = -\left(\frac{r_l}{r'_s}\right)\left(\frac{1 + r'^2_s}{1 + r_l^2}\right)$$

wherein $\beta$ is an amplitude of a total reflectance coefficient $r_{net}$ of the stack including the top layer, wherein the total reflectance coefficient is imaginary and has a form of $\pm j\beta$, wherein j is the imaginary unit and $\pm j = \sqrt{-1}$, and $r_s$ and $r_s'$ are the reflectance of the substrate and the plurality of bi-layers combined, calculated with air and the top layer as the ambient medium, respectively.

6. The apparatus of claim 5, wherein the plurality of thin films include a plurality of bi-layers, wherein each of the plurality of bi-layers comprises a layer of high refractive index and a layer of low refractive index.

7. The apparatus of claim 6, wherein the high refractive index is about 1.45-1.65, and the low refractive index is lower than the high refractive index.

8. The apparatus of claim 6, wherein the layer of high refractive index and the layer of low refractive index each have a thickness of approximately ¼ of the wavelength $\lambda$.

9. The apparatus of claim 1, wherein the apparatus is configured to sense or image a sample disposed over the stack through a change in reflectance caused by the presence of the sample.

10. The apparatus of claim 9, wherein the sample comprises one of a biological sample, a chemical material, or an optical material, and wherein the apparatus is configured as one of a biosensor, a chemical sensor, or a color sensor.

11. A method of making a sensor or an imager, the method comprising:
    selecting materials for a top layer, a plurality of thin films, and a substrate; and
    forming a stack with the top layer, the plurality of thin films, and the substrate,
    wherein the materials are selected such that stack has a substantially imaginary total reflectance for light at a wavelength $\lambda$ used for imaging or sensing, and
    wherein the substantially imaginary total reflectance coefficient is a total reflectance coefficient for which the real part of the reflectance is substantially zero, and the imaginary part of the reflectance is substantially non-zero.

12. The method of claim 11, wherein the plurality of thin films comprise polymer thin films.

13. The method of claim 11, wherein the forming comprises disposing the plurality of thin films as a plurality of bi-layers, wherein each of the plurality of bi-layers comprises a layer of high refractive index and a layer of low refractive index.

14. The method of claim 13, wherein the layer of high refractive index and the layer of low refractive index each have a thickness of approximately ¼ of the wavelength of the light used for sensing in the respective layer.

15. The method of claim 11, wherein the selecting comprises selecting a refractive index $(n_l)$, a thickness $(d_l)$, and a reflectance $(r_l)$ of the top layer such that they satisfy the following equations:

$$r'_s = \frac{r_s - r_l}{1 - r_s r_l} \text{ and } r_{net} = \frac{r_l + r'_s e^{-j2\phi_l}}{1 + r_l r'_s e^{-j2\phi_l}} = \pm j\beta$$

$$\frac{[r'_s(1 + r_l^2)]^2 - [r_l(1 + r'^2_s)]^2}{(1 - r_l^2 r'^2_s)^2} = \beta^2$$

$$\cos\left(4\pi \frac{n_l d_l}{\lambda}\right) = -\left(\frac{r_l}{r'_s}\right)\left(\frac{1 + r'^2_s}{1 + r_l^2}\right)$$

wherein β is an amplitude of a total reflectance coefficient $r_{net}$ of the stack including the top layer, wherein the total reflectance coefficient is imaginary and has a form of ±jβ, wherein j is the imaginary unit and $\pm j = \sqrt{-1}$, and $r_s$ and $r_s'$ are the reflectance of the substrate and the plurality of bi-layers combined, calculated with air and the top layer as the ambient medium, respectively, and wherein λ is the wavelength of the light used for imaging or sensing.

16. A method of sensing or imaging a sample, the method comprising:

providing a stack comprising a plurality of polymer thin films, wherein the stack has a substantially imaginary total reflectance for light at a wavelength λ used for imaging or sensing, wherein the substantially imaginary total reflectance coefficient is a total reflectance coefficient for which the real part of the reflectance is substantially zero, and the imaginary part of the reflectance is substantially nonzero;

directing a beam of light toward the stack in the absence of the sample;

measuring the reflectance of the stack in the absence of the sample;

disposing a sample over the stack;

measuring the reflectance of the stack in the presence of the sample; and obtaining the difference in reflectance of the stack in the presence and absence of the sample.

17. The method of claim 16, wherein the plurality of thin films include a plurality of bi-layers, wherein each of the plurality of bi-layers comprises a layer of high refractive index and a layer of low refractive index.

18. The method of claim 17, wherein the layer of high refractive index and the layer of low refractive index each have a thickness of approximately ¼ of the wavelength λ of the light used for imaging or sensing in the respective layer.

* * * * *

UNITED STATES PATENT AND TRADEMARK OFFICE
CERTIFICATE OF CORRECTION

PATENT NO. : 8,310,679 B2
APPLICATION NO. : 13/318601
DATED : November 13, 2012
INVENTOR(S) : Varma Page 1 of 3

It is certified that error appears in the above-identified patent and that said Letters Patent is hereby corrected as shown below:

On the Title Page, in Column 1, insert item (30),
-- Foreign Application Priority Data
Jan. 31, 2011 (IN).................288/CHE/2011 --.

On the Title Page, item (56), under "OTHER PUBLICATIONS", in Column 2, Line 3, delete "al," and insert -- al., --, therefor.

On the Title Page, item (56), under "OTHER PUBLICATIONS", in Column 2, Line 4, delete "Silicon". Nat. Biotech." and insert -- Silicon", Nat. Biotech., --, therefor.

On the Title Page, item (56), under "OTHER PUBLICATIONS", in Column 2, Line 6, delete "Instr." and insert -- Instr., --, therefor.

On the Title Page, item (56), under "OTHER PUBLICATIONS", in Column 2, Line 8, delete "al," and insert -- al., --, therefor.

On the Title Page, item (56), under "OTHER PUBLICATIONS", in Column 2, Lines 15-16, delete "Applications." and insert -- Applications, --, therefor.

On Title Page 2, item (56), under "OTHER PUBLICATIONS", in Column 1, Line 6, delete "Bioanal, Chem." and insert -- Bioanal. Chem., --, therefor.

On Title Page 2, item (56), under "OTHER PUBLICATIONS", in Column 1, Line 8, delete "Bioelec." and insert -- Bioelec., --, therefor.

On Title Page 2, item (56), under "OTHER PUBLICATIONS", in Column 1, Line 11, delete "Chemosensors"." and insert -- Chemosensors", --, therefor.

Signed and Sealed this
First Day of July, 2014

Michelle K. Lee
*Deputy Director of the United States Patent and Trademark Office*

CERTIFICATE OF CORRECTION (continued)

On Title Page 2, item (56), under "OTHER PUBLICATIONS", in Column 2, Line 3, delete "23:" and insert -- 23, --, therefor.

On Title Page 2, item (56), under "OTHER PUBLICATIONS", in Column 2, Line 5, delete "Multilayers" Nat. Matter." and insert -- Multilayers", Nat. Mater., --, therefor.

On Title Page 2, item (56), under "OTHER PUBLICATIONS", in Column 2, Line 13, delete "Diagn." and insert -- Diagn., --, therefor.

On Title Page 2, item (56), under "OTHER PUBLICATIONS", in Column 2, Line 15, delete "Biotechnol." and insert -- Biotechnol., --, therefor.

On Title Page 2, item (56), under "OTHER PUBLICATIONS", in Column 2, Line 18, delete "Chem. vol. 47:10" and insert -- Chem., vol. 47, 10 --, therefor.

In the Drawings

The drawing sheet, consisting of Fig. 8, should be deleted to be replaced with the drawing sheet, consisting of Fig. 8, as shown on the attached page.

In the Specification

In Column 5, Line 18, delete "$\lambda$," and insert -- $\lambda$ --, therefor.

In Column 9, Line 66, delete "$D_l$" and insert -- $D_i$ --, therefor.

In Column 11, Line 11, delete "$\alpha_m$" and insert -- $\alpha_{RIN}$ --, therefor.

In Column 12, Line 7, delete "material s" and insert -- materials --, therefor.

In Column 13, Line 53, delete "cereberospinal" and insert -- cerebrospinal --, therefor.

In Column 16, Line 41, delete "claim:" and insert -- claim, --, therefor.